United States Patent [19]

Janski et al.

[11] Patent Number: 4,888,416

[45] Date of Patent: Dec. 19, 1989

[54] METHOD FOR STABILIZING SOMATOTROPINS

[75] Inventors: Alvin M. Janski, Northbrook; Susan M. Drengler, Lindenhurst, both of Ill.

[73] Assignee: International Minerals & Chemical Corp., Northbrook, Ill.

[21] Appl. No.: 31,273

[22] Filed: Mar. 30, 1987

[51] Int. Cl.$^4$ .............................................. C07K 3/28
[52] U.S. Cl. .................................. 530/399; 530/402; 530/412; 530/427; 435/68; 435/70; 514/2; 514/8; 514/21; 514/975; 514/970
[58] Field of Search .............. 530/311, 402, 399, 412, 530/427; 435/68, 70; 514/975, 970, 21, 2, 8

[56] References Cited

U.S. PATENT DOCUMENTS

| | | | |
|---|---|---|---|
| 3,279,996 | 10/1966 | Long et al. | 167/82 |
| 3,634,258 | 1/1972 | Wildi et al. | 435/188 |
| 3,682,842 | 8/1972 | Innerfield | 435/188 |
| 3,845,770 | 11/1974 | Theeuwes et al. | 128/260 |
| 3,860,536 | 1/1975 | Landwerlen et al. | 435/188 |
| 4,190,048 | 2/1980 | Sampson | 128/215 |
| 4,306,553 | 12/1981 | Dorman et al. | 128/214 |
| 4,439,181 | 3/1984 | Blackshear et al. | 604/56 |
| 4,478,829 | 10/1984 | Landaburu et al. | 514/21 |
| 4,578,269 | 3/1986 | Morein | 424/89 |
| 4,604,377 | 8/1986 | Fernandes et al. | 514/2 |
| 4,623,717 | 11/1986 | Jernmdes et al. | 530/381 |
| 4,694,073 | 9/1987 | Bentle et al. | 530/399 |
| 4,717,717 | 1/1988 | Finkenaur | 514/21 |

FOREIGN PATENT DOCUMENTS

| | | | |
|---|---|---|---|
| 0103395 | 3/1984 | European Pat. Off. | 435/68 |
| 0104920 | 4/1984 | European Pat. Off. | 435/68 |
| 0102519 | 8/1980 | Japan . | |
| 0068787 | 4/1982 | Japan | 435/188 |

OTHER PUBLICATIONS

Putnam, Advances in Protein Biochemistry 4:79–122 (1948) "The Interactions of Proteins and Synthetic Detergents".

Reynolds, et al., Proc. Nat. Acad. Sci., 66:1002–1007; "Binding of Dodecyl Sulfate to Proteins at High Binding Ratios. Possible Implications for the State of Proteins in Biological Membranes".

*Primary Examiner*—Garnette D. Draper
*Attorney, Agent, or Firm*—Wendell Ray Guffey; Thomas L. Farquer

[57] ABSTRACT

A method for preparing a dried protein product, such that the bioactivity and potential for solubility of the protein are substantially maintained when said product is administered to a living being and contacted with body fluids of said being, which comprises:

(a) forming an aqueous solution comprising a mixture of said protein and an ionic detergent and (b) drying said protein-detergent mixture, wherein a sufficient amount of detergent is mixed with said protein in step (a) to substantially fully coat said protein.

36 Claims, No Drawings

METHOD FOR STABILIZING SOMATOTROPINS

TECHNICAL FIELD

This invention relates to a novel dried protein product wherein the potential for solubility and bioactivity of the protein are substantially maintained. The invention also relates to a method for preparing this novel product and to the administration of the product to a living being.

BACKGROUND OF THE INVENTION

In recent years, a variety of methods and devices have been disclosed for the administration of various beneficial agents, such as drugs or medicaments, to the body of a living being. For example, the agent may be dissolved in a fluid which is compatible with body tissues and body fluids and then administered to the living being by means of an intravenous tube. Alternatively, the agent in solution may be administered by means of an infusion pump. There are a number of patents which teach various types of infusion pumps. See, for example, U.S. Pat. No. 4,190,048, which discloses an apparatus having a reservoir which is implanted in the body of a living being and a pump which also is implanted. The pump can be refilled by injecting infusate through the skin of the patient, through a pump septum and into the chamber inside the apparatus.

Also well known are a number of devices which can be implanted inside the body of the living being and are constructed such that the beneficial agent can diffuse out of the device. For example, U.S. Pat. No. 3,279,996, issued to Long et al., discloses a method and means for the controlled release of a therapeutic agent into a living organism by implanting within the body of that organism a capsule formed of silicone rubber and containing a therapeutic agent soluble in and capable of diffusing through the rubber to its outer surface at a constant rate. Another patent, U.S. Pat. No. 3,845,770, issued to Theeuwes et al., is directed to an osmotic device for the controlled release of an agent which comprises a semi-permeable membrane that surrounds a compartment which contains the agent. The wall is permeable to an external body fluid but impermeable to the agent and has a passageway for delivering the agent to the body. To release the agent, fluid is imbibed through the wall into the compartment to produce a solution of the agent. That solution is dispensed through the passageway at a rate controlled by the permeability of the wall and the osmotic pressure gradient across the wall of the device.

Despite these and various other systems and devices for releasing beneficial agents, certain problems have remained. One problem is that certain beneficial agents, especially high molecular weight agents, such as some proteins, are unstable, insoluble or cannot be solubilized in body fluids or other aqueous-based solvents. As a result, when they are placed in a slow release delivery device and come into contact with body fluids or they are added to a solution for purposes of intravenous administration, they have a tendency to transform into insoluble aggregates.

Attempts have been made to solve this problem. For example, U.S. Pat. No. 4,439,181, issued to Blackshear, discloses a method for preventing the precipitation of solubilized insulin within an infusion pump-type of delivery system that depends on the fluidity of the insulin solution for proper function. Specifically, Blackshear discloses stabilizing the insulin by adding an effective amount of a polyol, such as glycerol, to the solution.

Similarly, U.S. Pat. No. 4,306,553, issued to Dorman, teaches adding specific detergents in low concentrations to an insulin solution to maintain the solution's fluidity.

Although the teachings of these two patents may be helpful in certain situations, further methods for stabilizing polypeptides are sought.

SUMMARY OF THE INVENTION

In accordance with the present invention there is disclosed a novel dried protein product and a method for making it. It surprisingly has been found that when an ionic detergent which will bind strongly with a protein is mixed with an aqueous solution of the protein, and the protein-detergent mixture is dried to form a dried product, the bioactivity and potential for solubility of the protein when it subsequently is contacted with an aqueous-based fluid are substantially maintained, provided the amount of detergent mixed with the protein is sufficient to substantially coat the protein. This invention also relates to the administration of the novel dried protein products to enhance a biological process in a living being.

DETAILED DESCRIPTION OF THE INVENTION

The present invention relates to a method of preparing a dried protein product such that when the dried product is placed in a delivery device which is inserted or implanted into the body of a living being, or added to a solution which is administered by means of an intravenous injection or an infusion pump, the protein will retain its bioactivity and will not significantly suffer from insolubility problems. Applicants have discovered that by mixing a sufficient amount of an ionic detergent with a bioactive protein to substantially fully coat the protein prior to drying the protein, then drying the protein-detergent mixture, the resultant dried product maintains its bioactivity and is not subject to significant insolubilization problems when administered to a living being and contacted with body fluids or other aqueous-based fluids.

The method of this invention can be used with a variety of high and low molecular weight polypeptides and proteins, in a dried form, that have a tendency to form aggregates that will not resolubilize after being wetted. The term "high molecular weight" is used herein to represent polypeptides having a molecular weight of at least about 10,000 daltons. As used herein, the term "protein" encompasses both natural and synthetic proteins and polypeptides, including those produced using recombinant DNA techniques. The term includes both full length polypeptides and proteins and biologically active derivatives and fragments thereof. A bioactive protein or polypeptide is one which, following administration to a living being, has a demonstrable effect on a biological process of that living being.

In a preferred embodiment of the invention the protein is an animal somatotropin such as bovine or porcine somatotropin (also sometimes referred to as growth hormone). Compositions containing bioactive somatotropins can be administered to animals to promote their rate of growth, feed efficiency, carcass composition and/or milk production. The somatotropin may be obtained in accordance with conventional techniques by isolation from excised pituitary tissue. Alternatively, the somatotropins can be produced from genetically engineered microorganisms containing recombinant DNA which specifies the production of a somatotropin. See, for example, European Patent Application 83304574.3 (publication number 0 103 395) to Biogen N.V. The procedures for making such somatotropins are known and are described, for example, in the aforementioned European patent application (which describes the production of bovine somatotropin) and European Patent Application No. 8335717.7 (publication number 0 104 920) which describes the production of porcine somatotropin.

Although somatotropins are somewhat species specific, there is considerable homology among the amino acid sequences of animal somatotropins, and they have been shown to exhibit inter-species activity. In addition, various active fragments of somatotropins have been discovered. As used herein, the term somatotropin is intended to include the full length natural or recombinant somatotropin as well as derivatives thereof that have growth-promoting capabilities. Derivatives include biologically active fragments of the polypeptide hormone, such as Δ4 and Δ9 constructions of bovine somatotropin (polypeptides missing 4 and 9 amino acids from the N-termini, respectively, and described in the Biogen European Patent Application No. 83304574.3) and a polypeptide designated Δ7 pST, which has an amino acid sequence corresponding to that of the full-length porcine somatotropin less the first seven amino acids of the mature polypeptide (described in European Patent Application No. 83305717.7). The term somatotropin also includes an active fragment of the polypeptide that comprises an extraneous N-terminal methionine.

Typical procedures for recovering and purifying somatotropins and other proteins result in aqueous solutions of the protein. By the method of this invention, prior to recovering the somatotropin, or other protein, from solution, an ionic detergent advantageously is provided for the protein. Desirably, the detergent is provided in amounts to coat the protein sufficiently to maintain the potential of the protein to solubilize after the coated protein has been dried and contacted with aqueous-based fluids, such as body fluids. Desirably, sufficient detergent is added such that the protein molecules will be substantially coated by the detergent. Generally, the detergent is added such that the weight to weight ratio of detergent to protein is at least about 40:60; preferably the weight to weight ratio of detergent to protein is about 50:50. It has been found that if insufficient detergent is added to substantially coat the protein, the protein's loss of potential to solubilize after it has been dried and contacted with body fluids may actually be heightened rather than diminished. Although not wishing to be bound by theory, it appears that the presence of a lesser amount of detergent allows the partial coating, and, thus, partial unfolding, of the protein. Subsequent contact with an aqueous fluid allows the uncoated, unfolded regions of the protein molecules to interact to a greater extent than the coated or folded regions, thereby increasing the relative amount of aggregation. If sufficient detergent is added, such that the protein molecules are substantially fully coated, however, the protein molecules cannot interact when wetted, and no significant aggregation can occur.

A variety of strong-binding ionic detergents can be used in the method of this invention. The term "strong-binding" is used herein to mean strong hydrophobic and/or ionic interactions. The selection of an anionic or cationic detergent will depend upon whether the protein of interest is characterized by available positive charges or negative charges. Preferred anionic detergents are alkylsulfates having the general formula $RO-SO_3M$, wherein R is an alkyl group generally having up to about 16 carbon atoms and M is a cation such as the sodium or potassium ion. An especially preferred anionic detergent is sodium dodecyl sulfate (SDS).

AFter the detergent has been mixed with the solution of protein, the mixture is dried. This step may be carried out in accordance with conventional techniques. A preferred technique is lyophilization.

The dried protein-detergent mixture, also referred to herein as the dried protein product, then can be administered to a living being. It may be administered for example, by adding it to a solution which will be administered by means of an intravenous injection or infusion pump in accordance with conventional techniques. In vitro experiments desired to simulate in vivo use of the dried protein product of this invention have shown that the presence of the detergent does not adversely affect the bioactivity of the protein.

The invention is further illustrated by the following examples which are not to be construed as limiting.

EXAMPLE 1

In Vitro Wetting

SDS was dissolved in a solution of 1 mg/ml recombinant porcine somatotropin (rpST) (made substantially in accordance with the teachings of Biogen's European Patent Application 83304574.3) and lyophilized, resulting in products which were 0%, 0.2%, 1%, 6%, 20% or 50% SDS (by weight).

Five mg portions of the lyophilized mixtures were wetted with 10 μl PBS (140 mM NaCl, 10 mM $Na_3HPO_4$, pH 7.4)+$NaN_3$ (0.2%) plus HCl (to adjust the wetted pH to 7.4) for 15 days at 37° C. The wetting procedure simulates the effects on the dried protein product when it is inserted in a delivery device, implanted in the body of a living being and contacted with body fluids. Unwetted samples were stored dry at −20° C. until day 15. The samples all were suspended in 1 ml of PBS+$NaN_3$, pH 7.4, then sonicated to disperse the pellets. The suspensions were transferred to larger tubes and diluted to 1 mg/ml ST. After 4 hours of solubilization, with hourly mixing by inversion at room temperature, 10 μl suspension aliquots were taken. The tubes were centrifuged 10 min at 1500×g before 10 μl supernatant aliquots were taken.

Samples were analyzed for protein content by the Pierce BCA protein assay (see Table 1).

A concentration dependence was reflected in solubilities after wetting. After 0 days of wetting, solubilities were high (83–104%) regardless of SDS concentration; however, after 15 days of wetting solubilities were <10% in all cases, except when 50% (w/w) SDS was present, a condition which resulted in an average solubility of 95.6%. The lower concentrations of SDS may have been detrimental, causing solubilities to be reduced from an average of 6.0% (in the absence of SDS) to 0% at 1, 6, or 20% SDS. In the case of 20% SDS, unlike the other conditions, pellets of insoluble ST were refractory to resuspension. AT 20% SDS, only partial coating of the ST molecule with SDS would be expected. It is theorized that regions of the ST molecule that are not coated in such a condition of partial coating, may have a greater tendency to unfold than the same regions in a case of a molecule of ST without bound SDS, because part of the stability of a properly folded molecule is contributed by many regions of the molecule. The coating of some of these regions with SDS would prevent their participation in the normal intramolecular interactions, resulting in destabilization (i.e. unfolding) of the uncoated regions. These unfolded regions of different ST molecules would have a tendency to interact and result in aggregation during wetting. This would imply that substantial coating of the protein molecule is necessary for the stabilizing effect of the detergent.

TABLE 1

Solubility of rpST After In Vitro Wetting in the Presence of SDS

| rpST Sample SDS Content (%, w/w) | Period of Wetting (Days)$^a$ | Solubility of rpST After Wetting (%)$^b$ |
|---|---|---|
| 0 | 0 | 93.1 |
| 0 | 15 | 4.1 |
| 0 | 15 | 6.4 |
| 0 | 15 | 7.4 |
| 0.2 | 0 | 97.0 |
| 0.2 | 0 | 98.0 |
| 0.2 | 15 | 0.8 |
| 0.2 | 15 | 4.4 |
| 1 | 0 | 104.0 |
| 1 | 0 | 94.9 |
| 1 | 15 | 0.0 |
| 1 | 15 | 0.0 |
| 6 | 0 | 93.7 |
| 6 | 0 | 83.0 |
| 6 | 15 | 0.0 |
| 6 | 15 | 0.0 |
| 20 | 0 | 101.0 |
| 20 | 0 | 87.1 |
| 20 | 15 | 0.0 |
| 20 | 15 | 0.0 |
| 50 | 0 | 104.0 |
| 50 | 0 | 96.4 |
| 50 | 15 | 91.7 |
| 50 | 15 | 99.5 |

$^a$"0 day" samples were stored dry at −20° C. for the 15-day period and then wetted for <1 min before solubilization in PBS.
$^b$"Solubilities" represent measurable rpST in supernatant fractions, after wetting for the given time periods, divided by solubility in the suspension fractions after 0 days of wetting.

EXAMPLE 2

Rat Growth Activity Measurements

Samples of recombinant porcine somatotropin, containing 0 or 50% SDS before or after wetting, were diluted to 30–120 μg/ml in Buffer A (0.15M NaCl, 0.03M NaHCO$_3$, pH 9.5). The solutions were stored refrigerated between injections.

110 rats were randomly assigned to 11 groups of 10 rats each. As shown in Table 2, one group was injected with 0.2 ml of Buffer A as a negative control. The other groups were injected with 0.2 ml of rpST solution, which contained 0 or 50% SDS, either before or after wetting. The injections were administered daily for 9 days. (The wetting procedure was as described in Example 1.) Rats were injected at 2 or 3 different doses (6, 12 or 24 μg/rat/day), as indicted in Table 2. Rats were weighed daily. Growth was calculated by the difference between rat weight on day 10 and the initial weight on day 1 (see Table 2).

At the high dose (24 μg/day), all rpST samples (wetted or unwetted, with or without SDS) caused significant increases in rat growth (as based on the results of a one-sided Dunnet's test, p<0.01; see table 2). At the low (6 μg/day) dose, rpST wetted in the presence of SDS caused a significant increase in rat growth, whereas that wetted in the absence of SDS did not result in a significant response. The bioactivity of rpST with 50% SDS was comparable before and after wetting. The data indicate SDS stabilized the growth activity of wetted rpST. These results also indicate that after injection, dissociation of bound SDS is sufficient to generate a bioactive rpST molecule.

TABLE 2

Effect of SDS on Stabilization of the Rat Growth Activity of rpST

| Sample Identity | Dose (μg) | Wt Gain (%) Mean | S.D. |
|---|---|---|---|
| Negative Control | 0 | 3.8 | 2.6 |
| rpST + 0% SDS (unwetted) | 6 | 7.2 | 1.9 |
|  | 12 | 10.4* | 2.8 |
|  | 24 | 11.3* | 1.3 |
| rpST + 0% SDS (wetted) | 6 | 4.7 | 2.8 |
|  | 24 | 10.4* | 1.9 |
| rpST + 50% SDS (unwetted) | 6 | 8.8* | 3.0 |
|  | 24 | 11.3* | 3.5 |
| rpST + 50% SDS (wetted) | 6 | 8.7* | 3.5 |
|  | 12 | 8.8* | 3.4 |
|  | 24 | 9.8* | 2.9 |

*Significantly different (P < 0.01) from negative control using a one-sided Dunnetts test following an analysis of variance. Therefore, these samples are considered biologically active.

We claim:

1. A method for preparing a dried natural or recombinant animal somatotropin product which comprises:
   (a) forming an aqueous solution comprising a mixture of a somatotropin and an ionic detergent which can bind strongly to the somatotropin, wherein the amount of the detergent is sufficient to substantially coat the somatotropin, and
   (b) drying the somatotropin-detergent mixture wherein the bioactivity and potential for solubility of the somatotropin are substantially maintained when the dried somatotropin-detergent mixture is contacted with an aqueous fluid.

2. The method of claim 1 wherein the weight to weight ratio of detergent to somatotropin is at least about 40:60.

3. The method of claim 1 wherein the weight to weight ratio of detergent to somatotropin is about 1:1.

4. The method of claim 1 wherein the ionic detergent is an anionic detergent.

5. The method of claim 1 wherein said detergent comprises an alkyl sulfate.

6. The method of claim 5 wherein the detergent is sodium dodecyl sulfate.

7. The method of claim 1 wherein the ionic detergent is a cationic detergent.

8. The method of claim 1 wherein the somatotropin-detergent mixture is dried by lyophilization.

9. The method of claim 1, wherein the somatotropin is recombinant porcine somatotropin.

10. The method of claim 9 wherein the somatotropin is Δ7 rpST.

11. The method of claim 1, wherein the somatotropin is recombinant bovine somatotropin.

12. The method of claim 11 wherein the somatotropin is Δ4 rbST.

13. The method of claim 11 wherein the somatotropin is Δ9 rbST.

14. A dried, bioactive somatotropin-detergent product made in accordance with the method of claim 1.

15. The product of claim 14 wherein the weight to weight ratio of detergent to somatotropin is at least about 40:60.

16. The product of claim 15 wherein the weight to weight ratio of detergent to somatotropin is about 1:1.

17. The product of claim 14 wherein the detergent is sodium dodecyl sulfate.

18. The product of claim 17 wherein the somatotropin is natural or recombinant porcine somatotropin.

19. The product of claim 17 wherein the somatotropin is natural or recombinant bovine somatotropin.

20. A dried bioactive natural or recombinant animal somatotropin product which comprises a mixture of a somatotropin and an ionic detergent, wherein the detergent is bound strongly to the somatotropin and the ratio of detergent to somatotropin is such that the somatotropin is substantially fully coated by the detergent, wherein the bioactivity and potential for solubility of the somatotropin are substantially maintained when the dried somatotropin-detergent mixture is contacted with an aqueous fluid.

21. The somatotropin product of claim 20 wherein the weight to weight ratio of detergent to somatotropin is at least about 40:60.

22. The somatotropin product of claim 21 wherein the weight to weight ratio of somatotropin to detergent is about 1:1.

23. The somatotropin product of claim 20 wherein the detergent is sodium dodecyl sulfate.

24. The somatotropin product of claim 23 wherein the somatotropin is recombinant porcine somatotropin.

25. The somatotropin product of claim 24 wherein the somatotropin is $\Delta 7$ rpST.

26. The somatotropin product of claim 23 wherein the somatotropin is recombinant bovine somatotropin.

27. The somatotropin product of claim 26 wherein the somatotropin is $\Delta 4$ rbST.

28. The somatotropin product of claim 26 wherein the somatotropin is $\Delta 9$ rbST.

29. A process for enhancing the rate of growth of a living being which comprises administering to the living being a growth-enhancing amount of a dried bioactive somatotropin product which comprises a mixture of a natural or recombinant animal somatotropin and an ionic detergent, wherein the detergent is bound strongly to the somatotropin and the ratio of detergent to somatotropin is such that the somatotropin is substantially fully coated by the detergent, wherein the bioactivity and potential for solubility of the somatotropin are substantially maintained when dried somatotropin-detergent mixture is contacted with an aqueous fluid.

30. The process of claim 29 wherein the somatotropin is recombinant porcine somatotropin.

31. The process of claim 29 wherein the somatotropin is recombinant bovine somatotropin.

32. The process of claim 29 wherein the dried somatotropin product is administered by dissolving it in a biologically acceptable fluid and injecting it into the body of a living being.

33. The somatotropin of claim 20 wherein the ionic detergent is an anionic detergent.

34. The somatotropin product of claim 20 wherein the detergent comprises an alkyl sulfate.

35. The somatotropin product of claim 34 wherein the detergent is sodium dodecyl sulfate.

36. The somatotropin product of claim 20 formed by lyophilization.

* * * * *

UNITED STATES PATENT AND TRADEMARK OFFICE
CERTIFICATE OF CORRECTION

PATENT NO. : 4,888,416

DATED : December 19, 1989

INVENTOR(S) : Alvin M. Janski and Susan M. Drengler

It is certified that error appears in the above-identified patent and that said Letters Patent is hereby corrected as shown below:

Column 4, line 11, "AFter" should read --After--

Column 4, line 65, "AT" should read --At--

Column 5, line 60, "indicted" should read --indicated--

Column 6, line 48, Claim 5, repalce "said" with --the--

Column 8, line 27, Claim 33, following "somatotropin" insert --product--

Signed and Sealed this

First Day of January, 1991

Attest:

HARRY F. MANBECK, JR.

Attesting Officer

Commissioner of Patents and Trademarks